United States Patent
Hull et al.

(10) Patent No.: US 9,095,846 B2
(45) Date of Patent: Aug. 4, 2015

(54) BIMETALLIC CATALYSTS FOR $CO_2$ HYDROGENATION AND $H_2$ GENERATION FROM FORMIC ACID AND/OR SALTS THEREOF

(75) Inventors: Jonathan F. Hull, Oakland, CA (US); Yuichiro Himeda, Ibaraki (JP); Etsuko Fujita, Port Jefferson, NY (US); James T. Muckeman, Port Jefferson, NY (US)

(73) Assignees: Brookhaven Science Associates, LLC, Upton, NY (US); National Institute of Advanced Industrial Science and Technology (AIST), Tokyo (JP)

( * ) Notice: Subject to any disclaimer, the term of this patent is extended or adjusted under 35 U.S.C. 154(b) by 0 days.

(21) Appl. No.: 14/240,587

(22) PCT Filed: Sep. 12, 2012

(86) PCT No.: PCT/US2012/054823
§ 371 (c)(1),
(2), (4) Date: Jun. 18, 2014

(87) PCT Pub. No.: WO2013/040013
PCT Pub. Date: Mar. 21, 2013

(65) Prior Publication Data
US 2014/0299817 A1 Oct. 9, 2014

Related U.S. Application Data

(60) Provisional application No. 61/533,950, filed on Sep. 13, 2011.

(51) Int. Cl.
*C07D 403/04* (2006.01)
*B01D 53/62* (2006.01)
(Continued)

(52) U.S. Cl.
CPC ........ *B01J 31/2295* (2013.01); *B01J 31/1815* (2013.01); *C01B 3/0015* (2013.01);
(Continued)

(58) Field of Classification Search
CPC ........... B01J 10/00; B01J 23/74; B01J 23/84; B01D 53/62; C07D 403/04
USPC ..................... 514/252.02; 544/238
See application file for complete search history.

(56) References Cited

U.S. PATENT DOCUMENTS 5,395,844 A 3/1995 Duncia et al.
5,661,108 A 8/1997 Crawford et al.
(Continued)

FOREIGN PATENT DOCUMENTS

EP 0618188 A2 10/1994
EP 2163553 A1 3/2010

OTHER PUBLICATIONS

Himeda "Highly efficient hydrogen evolution by decomposition of formic acid using an iridium catalyst with 4,4'-dihydroxy-2,2'-bipyridine" 2009, Green Chemistry, 11, 2018-2022.*
(Continued)

*Primary Examiner* — Stanley Silverman
*Assistant Examiner* — Syed Iqbal
(74) *Attorney, Agent, or Firm* — Hoffmann & Baron, LLP

(57) ABSTRACT

The invention relates to a ligand that may be used to create a catalyst including a coordination complex is formed by the addition of two metals; Cp, Cp* or an unsubstituted or substituted π-arene; and two coordinating solvent species or solvent molecules. The bimetallic catalyst may be used in the hydrogenation of $CO_2$ to form formic acid and/or salts thereof, and in the dehydrogenation of formic acid and/or salts thereof to form $H_2$ and $CO_2$.

40 Claims, 3 Drawing Sheets

(51) Int. Cl.
| | |
|---|---|
| B01J 31/22 | (2006.01) |
| C07D 239/56 | (2006.01) |
| C07D 239/48 | (2006.01) |
| C07D 239/52 | (2006.01) |
| C07D 239/58 | (2006.01) |
| C01B 3/00 | (2006.01) |
| C07C 51/15 | (2006.01) |
| B01J 31/18 | (2006.01) |

(52) U.S. Cl.
CPC ............ *C07C 51/15* (2013.01); *C07D 239/48* (2013.01); *C07D 239/52* (2013.01); *C07D 239/56* (2013.01); *C07D 239/58* (2013.01); *C07D 403/04* (2013.01); *B01J 2231/625* (2013.01); *B01J 2531/0216* (2013.01); *B01J 2531/821* (2013.01); *B01J 2531/822* (2013.01); *B01J 2531/824* (2013.01); *B01J 2531/825* (2013.01); *B01J 2531/827* (2013.01); *B01J 2531/828* (2013.01); *B01J 2531/842* (2013.01); *B01J 2531/845* (2013.01); *B01J 2531/847* (2013.01); *Y02E 60/324* (2013.01)

(56) References Cited

U.S. PATENT DOCUMENTS

| | | |
|---|---|---|
| 2007/0036706 A1 | 2/2007 | Ogo et al. |
| 2010/0168120 A1* | 7/2010 | Watterson et al. ....... 514/252.02 |
| 2012/0321550 A1 | 12/2012 | Fukuzumi et al. |
| 2013/0338159 A1* | 12/2013 | Cornella Taracido et al. ........................ 514/235.8 |

OTHER PUBLICATIONS

Loges et al., "Catalytic Generation of Hydrogen from Formic Acid and its Derivatives: Useful Hydrogen Storage Materials," Top Catal (2010) 53: 902-914.

* cited by examiner

BIMETALLIC CATALYSTS FOR $CO_2$ HYDROGENATION AND $H_2$ GENERATION FROM FORMIC ACID AND/OR SALTS THEREOF

This application claims priority based on an International Application filed under the Patent Cooperation Treaty, PCT/US2012/054823, filed Sep. 12, 2012, which claims priority from U.S. Provisional Application No. 61/533,950, filed Sep. 13, 2011, each of which are incorporated herein by reference.

This invention was made with Government support under contract number DE-AC02-98CH10886, awarded by the U.S. Department of Energy. The Government has certain rights in the invention.

BACKGROUND

The efficient and catalytic reduction of carbon dioxide, $CO_2$, by oxygenic photosynthetic organisms has inspired a variety of sustainable energy and chemical-feedstock applications because $CO_2$ is a cheap, abundant, and stable molecule. $CO_2$ is also a greenhouse gas, so its fixation as part of a carbon-neutral energy cycle would significantly decrease the environmental risks associated with greenhouse gases. Obtaining methane or methanol by the chemical reduction of $CO_2$ is desirable, but the strenuous kinetic requirements have thus far been prohibitive.

The inventors have therefore focused their attention on the partial reduction of $CO_2$ to formic acid as an energy-storage medium, because formic acid is able to store $H_2$ in liquid form and is a net carbon-neutral fuel, as shown below in Scheme 1. Hydrogen-storage media are also increasing in importance as research on $H_2$-releasing processes such as water oxidation and artificial photosynthesis intensifies.

Scheme 1. Hydrogen storage and release using $CO_2$ in water. The reaction equilibrium, $K_{EQ}$, may be shifted by adjusting the solution pH.

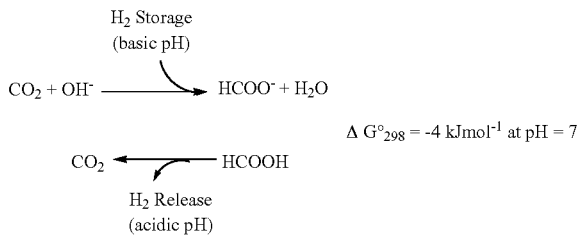

Water is an attractive solvent because it is benign and because the aqueous reaction is exergonic ($\Delta G°_{298}=-4$ kJmol$^{-1}$ at pH=7), while it is endergonic in the gas phase ($\Delta G°_{298}=+33$ kJmol$^{-1}$). However, despite several decades of research nearly all reported catalytic systems require extreme temperatures and pressures as well as organic additives to achieve satisfactory turnover numbers and reaction rates for both reaction directions.

Thus, there is a need for a catalyst that provides satisfactory turnover numbers and reaction rates for both reactions and does not require extreme temperatures and pressures or the presences of organic additives.

SUMMARY

One aspect relates to a ligand represented by formula I below:

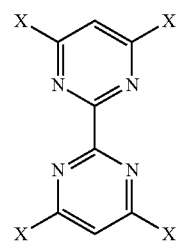

wherein X is independently OH, SH, or $NH_2$. Preferably, X is OH.

Another aspect relates to a catalyst of formula II below:

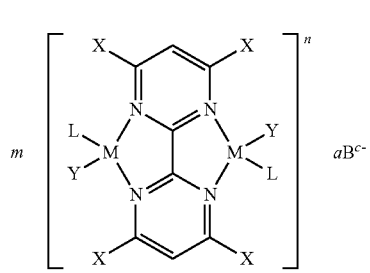

wherein X is independently OH, SH, or $NH_2$; M independently represents Ni, Pd, Pt, Co, Rh, Ir, Fe, Ru, or Os; Y independently represents a coordinating solvent species or solvent molecule selected from the group consisting of halide, water, hydroxyl, carbonyl, acetonitrile, dimethylformamide, and dimethylsulfoxide; L independently represents Cp, Cp*, or an unsubstituted or substituted n-arene; m and c independently represent integers from 1 to 6; n represents 0, +1, +2, +3, +4, +5, or +6; a represents an integer from 0 to 6; B represents an anion; and m×n=a×c.

Preferably M is Ir. In another preferred embodiments, Y is Cl. In yet another preferred embodiment, L is Cp, Cp*, benzene, or cymene.

The bimetallic catalysts may be used in a method of hydrogenating $CO_2$ to form formic acid and/or a salt thereof comprising reacting $CO_2$ and $H_2$ in water in the presence of a catalyst of formula II below and a base. The catalyst of formula II is described above.

Preferably, the hydrogenation reaction occurs at ambient pressure and ambient temperature. In another preferred embodiment, the reaction occurs in the absence of organic additives.

In one embodiment, the reaction occurs at a minimum pH of 5. The reaction may also occur at a maximum pH of 10. In another embodiment, the reaction occurs at a pH of about 8.

The bimetallic catalysts may also be used in a method of dehydrogenating formic acid and/or a salt thereof to form $H_2$ and $CO_2$ comprising reacting formic acid and/or a salt thereof in the presence of a catalyst of formula II. The catalyst of formula II is described above.

Preferably, the dehydrogenation reaction occurs between a minimum of 0° C. and a maximum of 200° C., more preferably between a minimum of 10° C. and a maximum of 80° C., and most preferably between a minimum of 40° C. and a maximum of 80° C.

In another embodiment, the reaction occurs at a maximum pH of 8.

In another embodiment, the dehydrogenation reaction occurs between a minimum of 0 MPa and a maximum of 1000 MPa. More preferably the reaction occurs between a minimum of 0.1 MPa and a maximum of 10 MPa. Preferably, the reaction occurs in the absence of organic additives.

The bimetallic catalysts may also be used in a method of reversibly storing hydrogen, the method comprising the steps of a) providing $H_2$ and $CO_2$ in water; b) adjusting the pH to a minimum of 5 at a temperature and pressure sufficient to produce formic acid and/or a salt thereof; and c) adjusting the pH to a maximum of 8 at a temperature and pressure sufficient to dehydrogenate the formic acid and/or a salt thereof to produce $H_2$ and $CO_2$; wherein steps b) and c) are conducted in the presence of a catalyst of formula II.

Preferably, steps a), b), and c) are conducted in a closed reaction vessel. In another preferred embodiment, steps b) and c) are repeated.

Preferred conditions for the hydrogenation and dehydrogenation reactions in steps b) and c), respectively, are as described above.

DETAILED DESCRIPTION

Figure 1:
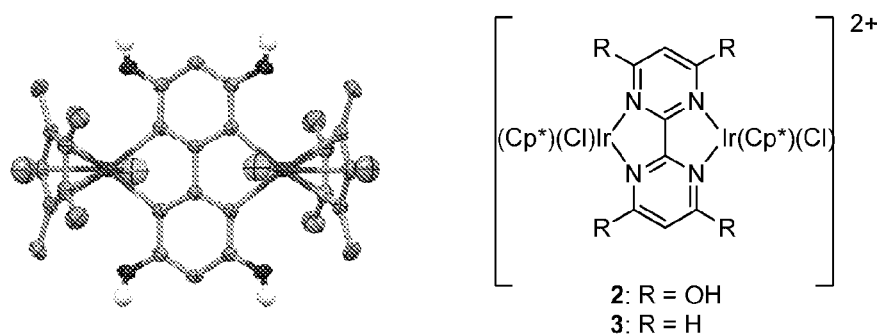
FIG. 1 shows the thermal ellipsoid plot of [{Ir(Cp*)(Cl)}$_2$(thbpym)](Cl)$_2$, 2, crystallized from aqueous Na$_2$SO$_4$. C—H bonds are omitted for clarity (Left) and the close structural resemblance of catalysts 2 and 3 (Right). Catalyst 3, which has no pendent base and cannot be deprotonated, is used to demonstrate the significant role that H-bonding plays in $CO_2$ reduction in this system.

One aspect of the present bimetallic catalysts relates to a ligand represented by formula I below:

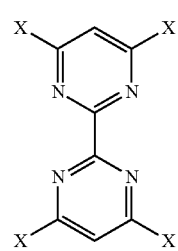

I wherein X independently is OH, SH, or NH$_2$.

The ligands of formula I may be transformed into a catalyst when a coordination complex is formed by the addition of two metals, a substituted or unsubstituted n-arene, and two coordinating solvent species.

The present catalysts are shown in formula II below:

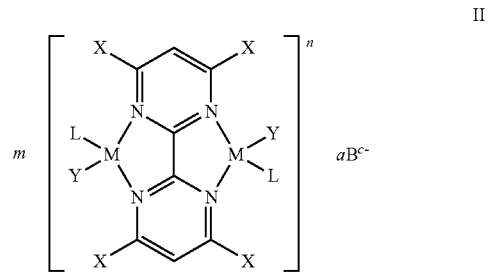

II

X is independently OH, SH, or NH$_2$, as defined above. X is preferably OH.

M independently represents a metal selected from Ni, Pd, Pt, Co, Rh, Ir, Fe, Ru, and Os. The term "independently" denotes that each M may be the same or different metal. For example, one catalyst may contain Fe and Ir. Preferably, both metals M in the catalyst are Ir.

Y independently represents a coordinating solvent species or solvent molecule selected from the group consisting of halide, water, hydroxyl, carbonyl, acetonitrile, dimethylformamide, and dimethylsulfoxide. Halides include fluoride, chloride, bromide, and iodide. Y is preferably chloride.

L independently represents pentamethylcyclopentadienyl (Cp*); cyclopentadienyl (Cp); or an unsubstituted or substituted π-arene. π-arenes are well known in the art.

In one aspect of the present bimetallic catalyst, the n-arenes are carbocyclic aromatic groups having, for example, 6 to 24 carbon atoms in one or more aromatic rings; heterocyclic-aromatic (heteroaromatic) groups having, for example, 5 to 30 carbon or heterocyclic atoms in one or more aromatic rings; or combinations of such carbocyclic aromatic groups and heterocyclic-aromatic groups. Heterocyclic atoms include oxygen, sulfur, or nitrogen. The nitrogen may be double bonded (i.e. —N=) or single bonded (i.e., part of an —N(H)— group). The n-arenes may be unsubstituted or substituted with one or more nitro groups, hydroxyl groups, halogen atoms, preferably chlorine or bromine atoms, or by $C_1$-$C_8$-alkyl, $C_1$-$C_8$ alkoxy, cyano, unsubstituted amino, $C_1$-$C_8$ alkylamino, $C_1$-$C_8$ alkylthio, $C_2$-$C_6$ monocarboxylic acid alkyl ester, phenyl, $C_2$-$C_5$-alkanoyl or benzoyl groups.

Examples of unsubstituted π-arenes include, but are not limited to, benzene, toluene, xylenes, ethyl benzene, cumene, methoxybenzene, ethoxybenzene, dimethoxybenzene, p-chlorotoluene, m-chlorotoluene, chlorobenzene, bromobenzene, dichlorobenzene, trimethylbenzene, trimethoxybenzene, naphthalene, 1,2-dihydronaphthalene, 1,2,3,4-tetrahydronaphthalene, methylnaphthalene, methoxynaphthalene, ethoxynaphthalene, chloronaphthalene, bromonaphthalene, biphenyl, stilbene, indene, 4,4'-dimethylbiphenyl, fluorene, phenanthrene, anthracene, 9,10-dihydroanthracene, triphenyl, pyrene, perylene, naphtacene, coronene, thiophene, chromene, xanthene, thioxanthene, benzofuran, benzothiophene, naphthothiophene, thianthrene, diphenylene oxide, diphenylene sulfide, acridine, pyrrole, pyridine, pyrimidine, and carbazole.

Preferably, the n-arene is hexamethylbenzene, i.e., $C_6(CH_3)_6$; benzene, i.e., $C_6H_6$; cymene, i.e., 1-methyl-4-(1-methylethyl)benzene; or a benzene derivatives such as a substituted benzene.

In formula II, the letters m and c independently represent integers from 1 to 6, i.e., 1, 2, 3, 4, 5, or 6. Therefore, m and c may be the same integer or different integer.

The letter n represents 0, +1, +2, +3, +4, +5, or +6. When n is +1, +2, +3, +4, +5, or +6 (or is not zero), then n is a valence of $1^+$, $2^+$, $3^+$, $4^+$, $5^+$, or $6'$, respectively.

The letter a represents an integer from 0 to 6, i.e., 0, 1, 2, 3, 4, 5, or 6.

The letters $aB^{c-}$ in formula II, represent the number and identity of anions necessary to maintain a charge-neutral compound. B represents any anion having a valence (c) of 1-6. Some examples of anions include, but are not limited to, monovalent anions such as halides (e.g., $F^-$, $Cl^-$, $Br^-$, and $I^-$), $OH^-$, and $H^-$ divalent anions such as $S^{2-}$, $CO_3^{2-}$, $SO_4^{2-}$, and trivalent anions such as $PO_4^{3-}$.

When a is 0, then no anion is present and the compound is already charge-neutral.

In order to maintain a charge-neutral compound, the letters m, n, a, and c are chosen so that m×n=a×c. For example, in the case where the compound is already charge-neutral, then n represents 0, m represents 1, a represents 0, and no anion is present.

In another aspect, the invention relates to a method of hydrogenating carbon dioxide ($CO_2$) to form formic acid and/or a salt thereof by reacting $CO_2$ and $H_2$ in water in the presence of a catalyst of formula II as described above and a base.

In a preferred embodiment, the reaction occurs in the absence of organic additives. Organic additives are well known in the art. Examples of organic additives commonly used along with catalyst, but preferably not included in the method of the invention include, but are not limited to, $NEt_3$, $NHMe_2$, $NEt_3/C_6F_5OH$, AcOH, $Me_2CO$, $MeCO_2$, $Me_2NHex$, citrate, and TEA.

In a preferred embodiment, an inorganic base is used in the hydrogenation reaction. Suitable inorganic bases for use in the hydrogenation reaction include but are not limited to, LiOH, NaOH, KOH, $Ca(OH)_2$, $Ba(OH)_2$, $Sr(OH)_2$, $Li_2CO_3$, $Na_2CO_3$, $K_2CO_3$, $CaCO_3$, $BaCO_3$, $SrCO_3$, $LiHCO_3$, NaHCO3, and $KHCO_3$. In a preferred embodiment, the concentration of inorganic base is within the range from about 1M to about 2M. This range encompansses any concentration in between and any concentration range in between.

A suitable pH of the hydrogenation reaction may be determined by a person having ordinary skill in the art. For example, the reaction may occur at a minimum pH of 5, 6, 7, 8, 9, or any number in between. For example, the reaction may occur at a minimum pH of 6.4. A preferred minimum pH is 5.

The hydrogenation reaction may occur at a maximum pH of 6, 7, 8, 9, 10, or any number in between. For example, the reaction may occur at a maximum pH of 8.9. Preferred maximum pH's are 9 and 10.

Each minimum pH may be combined with each maximum pH to create a feasible pH range within which the reaction may occur. For example, the reaction may occur at a minimum pH of 5.3 and a maximum pH of 8.9. In this example, the reaction would occur at any pH within the range of from 5.3 to 8.9.

In another aspect, the invention relates to a method of dehydrogenating formic acid and/or a salt thereof to form $H_2$ and $CO_2$ by reacting formic acid and/or a salt thereof in the presence of a catalyst of formula II as described above. The dehydrogenation reaction may occur at a minimum temperature of 0° C., 10° C., 20° C., 30° C., 40° C., 50° C., or any number in between. For example, the reaction may occur at a minimum temperature of 25.6° C. Preferred minimum temperatures are 0° C., 10° C., and 40° C.

The hydrogenation and dehydrogenation reactions may occur at a maximum temperature of 50° C., 60° C., 70° C., 80° C., 90° C., 100° C., 120° C., 140° C., 160° C., 180° C., 200° C. or any number in between. For example, the reaction may occur at a maximum temperature of 165° C. Each temperature minimum may be combined with each temperature maximum to create a feasible range of temperatures at which the reaction may occur. For example, the reaction may occur at a minimum temperature of 10° C. and a maximum temperature of 90° C. In this example, the reaction would occur at any temperature within the range of from 10° C. to 90° C.

The hydrogenation and dehydrogenation reactions may occur at ambient, reduced, or elevated temperatures and pressures. In another preferred embodiment, the hydrogenation and dehydrogenation reactions occur between a minimum of 0 MPa and a maximum of 1000 MPa. In yet another preferred embodiment, the reactions occur between a minimum of 0.1 MPa and a maximum of 10 MPa.

In a preferred embodiment, the dehydrogenation reaction occurs between a minimum of 10° C. and a maximum of 80° C.

In a preferred embodiment, the dehydrogenation reaction occurs between a minimum of 40° C. and a maximum of 80° C.

In a preferred embodiment, the dehydrogenation reaction occurs between a minimum of 0.1 MPa and 10 MPa.

An advantage of the present invention is that in a preferred embodiment, the hydrogenation reaction occurs at ambient pressure and ambient temperature.

Ambient pressure is defined as a pressure range of between a minimum of about 0.01 MPa and maximum of about 1 MPa. This range encompasses any pressure range in between, and any pressure in between.

Ambient temperature is defined as a temperature range of between a minimum of about 0° C. and maximum of about 100° C. This range encompasses any temperature range in between, and any temperature in between.

A suitable pH of the dehydrogenation reaction may be determined by a person having ordinary skill in the art. For example, the reaction may occur at a minimum pH of <1, 1, 2, or 3, or any number in between. For example, the reaction may occur at a minimum pH of 2.5. A preferred minimum pH is 3.

The reaction may occur at a maximum pH of 3, 4, 5, 6, 7, 8, or any number in between. For example, the reaction may occur at a maximum pH of 4.5. A preferred maximum pH is 4.

Each minimum pH may be combined with each maximum pH to create a feasible range of pH's where the reaction may occur. For example, the reaction may occur at a minimum pH of 3 and a maximum pH of 3.7. In this example, the reaction would occur at any pH from 3 to 3.7. A preferred pH is about 3.6.

In another aspect, the present catalysts are used in a method of reversibly storing hydrogen, the method including the steps of:

a) providing $H_2$ and $CO_2$ in water;

b) adjusting the pH to a minimum of 5 at a temperature and pressure sufficient to produce formic acid and/or a salt thereof; and c) adjusting the pH to a maximum of 8 at a temperature and pressure sufficient to dehydrogenate the formic acid and/or a salt thereof to produce $H_2$ and $CO_2$;

wherein steps b) and c) are conducted in the presence of a catalyst of formula II as described above.

Step b) is the hydrogenation process described above. Step c) is the dehydrogenation process described above. Any of the temperatures, pH values, and pressures discussed above in the hydrogenation and dehydrogenation processes may be substituted in the method of reversibly storing hydrogen. Preferably, the pH of the hydrogenation process is greater than the pH of the dehydrogenation process.

In a preferred embodiment, the method of reversibly storing hydrogen is conducted in a closed reaction vessel where steps b) and c) may be repeated. Preferably, the reactions occur in the absence of organic additives.

In a preferred embodiment, the temperature in step c) is adjusted to between a minimum of 10° C. and a maximum of 80° C.

In another preferred embodiment, the temperature in step c) is adjusted to between a minimum of 40° C. and a maximum of 80° C.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, with the present catalysts, groups of various parameters are defined (e.g. X, M, Y, and L). Each group contains multiple members. For example, the group X independently represents members OH, SH, or $NH_2$. Each member may be combined with each other member to form additional sub-groups, e.g., OH and SH, OH and $NH_2$, and SH and $NH_2$.

The instant catalysts further contemplates embodiments in which each element listed under one group may be combined with each and every element listed under any other group. For example, the group M is identified about as independently representing a metal selected from Ni, Pd, Pt, Co, Rh, Ir, Fe, Ru, and Os as members. Group Y is identified above as independently representing a coordinating solvent species or solvent molecule selected from the group consisting of halide, water, hydroxyl, carbonyl, acetonitrile, dimethylformamide, and dimethylsulfoxide as members. Each member element of M (Ni, Pd, Pt, Co, Rh, Ir, Fe, Ru, or Os) can be combined with each and every member element of Y (halide, water, hydroxyl, carbonyl, acetonitrile, dimethylformamide, or dimethylsulfoxide). For example, in one embodiment, M may be Ni and Ru, and Y may be hydroxyl and chloride. Alternatively, M may be Co and Ir, and Y may be water, etc. Similarly, a third group is L, in which the member elements are defined as independently representing Cp, Cp*, or an unsubstituted or substituted π-arene. Each of the above embodiments may be combined with each and every element of L. For example, in the embodiment wherein M is Pt and Ir, and Y is dimethylsulfoxide, L may be Cp* (or any other chemical moiety within the element of L).

With each group, it is specifically contemplated that any one or more members can be excluded. For example, if M is defined as Ni, Pd, Pt, Co, Rh, Ir, Fe, Ru, or Os, it is also contemplated that M is defined as Ni, Rh, Ir, or Fe.

The present catalyst compounds are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least one week.

Reaction Schemes

As illustrated in the bottom of Scheme 2 for the embodiment in which all X substituents are hydroxyl groups, the new catalyst combines (a) four "proton responsive" hydroxyl moieties $[\{Ir(Cp^*)(OH_2)\}_2(thbpym)]^{4+}$ in its 2 (protonated) and 2' (deprotonated) forms, with (b) a "proton relay" to act as a proximal pendent base for $H_2$ activation, in 2 and 2' respectively. One possibility for this interaction is shown in Scheme 3.

Scheme 2. Protonated and deprotonated forms of catalysts 1 and 2.
Once the pendent OH is deprotonated to O⁻, the ligand becomes strongly donating, and has a pendent base close to the metal coordination sphere. $L_n$ indicates a generic ligand set, and is discussed below along with the ligand pKa values.

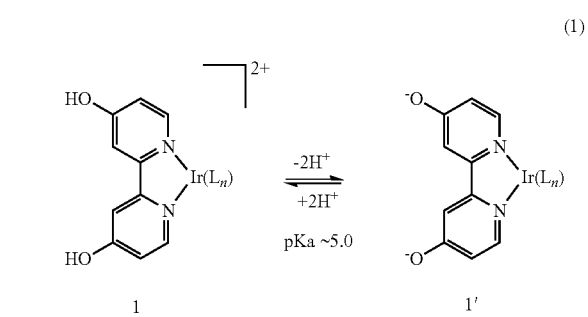

(1)

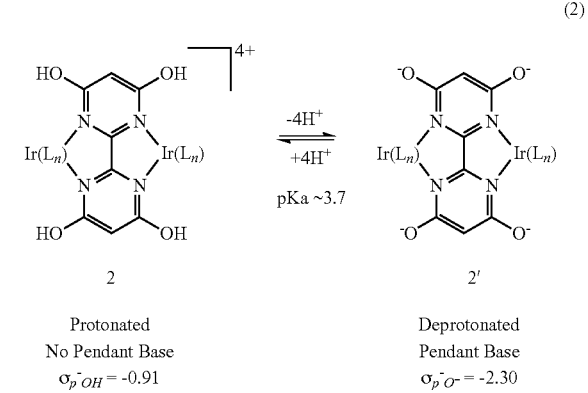

(2)

Protonated
No Pendant Base
$\sigma_p^-{}_{OH} = -0.91$

Deprotonated
Pendant Base
$\sigma_p^-{}_{O^-} = -2.30$

Scheme 3. The O⁻ oxyanion both electonically activates 2 and serves as a base/proton relay. $L_n$ indicates a generic ligand set; charges are omitted for clarity.

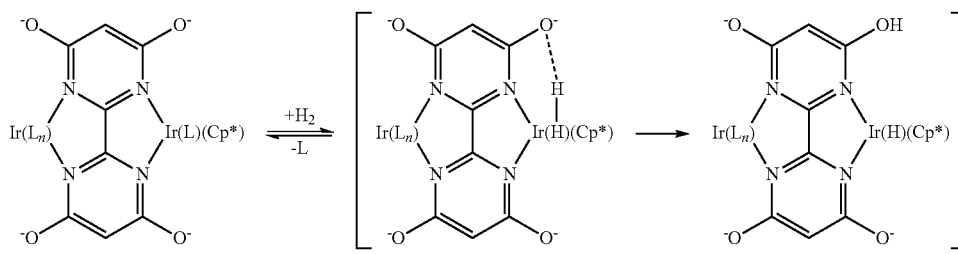

Catalyst 2, via 2', is a novel di-Iridium catalyst for the pH-controlled reversible hydrogenation of $CO_2$ or bicarbonate ($HCO_3^-$) to produce formic acid, and undergoes high turnovers at ambient temperature and pressure. Solutions having a pH>5 with deprotonated 2' are suitable for hydrogenation; the decomposition (dehydrogenation) of formic acid ($HCO_2H$) and formate ($HCOO^-$) using protonated 2 is suitable under acidic conditions, e.g., pH=<5, preferably <about 4, more preferably about 3.5-3.7, most preferably about 3.6. This "pH-switch" is derived from the multifunctional character of the ligand and provides the ability to turn $H_2$ production or consumption on or off by the addition of acid or base to the catalyst solution. The catalysts 2 or 2' can continuously consume or produce identical mixtures of $H_2$ and $CO_2$ at ambient pressure, and produce a high pressure mixture of $H_2$ and $CO_2$ (up to 5.0 MPa) simply by adjusting the solution pH. Catalyst 2 is the most active homogeneous catalyst yet reported for generating $H_2$ from formic acid (TOF=155,000 $h^{-1}$).

EXAMPLES

Synthesis and Structure

The thbpym ligand is obtained by reducing 4,4',6,6'-tetramethoxy-2,2'-bipyrimidine. 2 is prepared by stirring a 1:1 mixture of $[Cp*IrCl_2]_2$ and thbpym in methanol. Layering a methanolic solution of 2 onto concentrated $Na_2SO_4$ gave air-stable crystals suitable for X-ray diffraction (FIG. 1). The crystal structure shows two iridium atoms, each coordinated to a Cp* ligand, a chloride ligand and to two nitrogen atoms of the bridging ligand to form a dimer. The Ir—N bond lengths are similar to those in 3, $[\{Ir(Cp*)(Cl)\}_2(bpym)]^{2+}$ (bpym=2,2' bipyrimidine; FIG. 1). Catalyst 3 was synthesized and compared to 2 because it is structurally similar but has no hydroxyl groups, and the catalytic rates were compared in the catalysts with and without a pendent base.

Preparation of 4,4',6,6'-tetrahydroxypiyrimidine (thbpym)

4,4',6,6'-tetramethoxypiyrimidine (2.0 g, 7.19 mmol) was place into a 100-mL Schlenk flask, equipped with a stir bar, reflux condenser, and a vacuum adapter with a Teflon stopcock and dissolved in anhydrous acetonitirile (50 mL) under an Ar atmosphere. Trimethylsilyliodide (10.2 mL, 10 eq. 71.9 mmol) was added through the top of the reflux condenser, and the solution was refluxed for 16 h. The darkened solution was cooled to room temperature and the crude product was precipitated with MeOH (25 mL) filtered, and washed with MeOH (3×30 mL) and ether (3×30 mL). The crude material was purified by heating a slurry of the solid in in iPrOH (50 mL) to 50° C. for 1 h and cooling with an ice bath, after which it was filtered and washed successively with cold (about 5-10° C.) iPrOH (3×15 mL), MeOH (3×15 mL), and ether (3×15 mL). The resulting light yellow powder was dried at 50° C. for 24 h under high vacuum. Yield 1.51 g (94.6%). $^1H$ NMR ($d^6$-DMSO): 11.92 (bs, 4H), 5.64 (s, 2H), $^{13}C$ NMR ($d^6$-DMSO): 167.67, 153.17, 90.96. HRESI-MS calc. for $C_8H_7N_4O_4$: 223.0462 $(M+H)^+$. found 223.0456.

Preparation of $[\{Ir(Cp*)(Cl)\}_2(thbpym)](Cl_2)$, (2Cl)

A methanol solution (10 mL) of $[Cp*IrCl_2]_2$ (162 mg, 0.20 mmol) and 4,4',6,6'-tetrahydroxy-2,2'-bipyrimidine (45 mg, 0.20 mmol) was stirred at 40° C. for 12 h. The resulting precipitate was filtered to give a pale yellow solid (150 mg, 74%). Purification was carried out by reprecipitation of aqueous NaOH (1.25 eq) solution of 2 by addition of HCl (1.25 eq).

IR (KBr) 1633, 1476, 1375, 1274 $cm^{-1}$;
$^1H$ NMR ($D_2O$/KOD, 400 MHz) δ 5.34 (s, 2H), 1.55 (s, 30H);
$^{13}C$ NMR ($D_2O$/KOD, 100 MHz) δ 174.13, 168.89, 95.13, 87.55, 11.57;
Anal. Calcd for $C_{28}H_{36}Cl_4Ir_2N_4O_4O_4 \cdot 2/3H_2O$: C, 32.79; H, 3.67; N, 5.46. Found: C, 32.89; H, 4.07; N, 5.14.
ESIMS (NaOH aq.): m/z: 873 $[M-5H-4Cl]^-$.

Preparation of $[\{Ir(Cp*)(H)\}_2(thbpym)]$, (5)

Complex 2Cl (10 mg) was dissolved in 0.5 mL of KOD/$D_2O$ solution (pH 11). After a freeze-pump-thaw degassing, the solution was held under $H_2$ (0.4 MPa) for 8 h.
$^1H$ NMR ($D_2O$/KOD, 500 MHz): δ 5.23 (s, 2H), 1.67 (s, 30H), −10.70 (s, 2H).
$^{13}C$ NMR ($D_2O$/KOD, 125 MHz): δ 174.48, 168.04, 91.84, 89.99, 12.25.

Preparation of $[\{Rh(Cp*)(Cl)\}_2(thbpym)](Cl_2)$

To a mixture of 4,4',6,6'-tetrahydroxy-2,2'-bipyrimidine (35.9 mg, 0.16 mmol) and $[Cp*RhCl_2]_2$ (100 mg, 0.16 mmol), 10 mL of MeOH was added under an argon atmosphere. After stirring at 40° C. for 12 h, the reaction solution was filtered. The filtrate was evaporated, and the residual was dried under vacuum at 50° C. for 12 h. Yield: 114 mg red solid (83.8%). $^1H$ NMR ($D_2O$+NaOD, 500 MHz): δ 5.36 (s, 2H), 1.56 (s, 30H).

Preparation of $[\{Ru(C_6(CH_3)_6)(Cl)\}_2(thbpym)](Cl_2)$

To a mixture of 4,4',6,6'-tetrahydroxy-2,2'-bipyrimidine (33.2 mg, 0.15 mmol) and $[C_6(CH_3)_6RuCl_2]_2$ (100 mg, 0.15 mmol) 10 mL MeOH was added under an argon atmosphere.

After stirring at 40° C. for 12 h, the reaction solution was filtered. Filtrate was evaporated, the residual was dried under vacuum at 50° C. for 12 h. Yield 83 mg brown solid (62.4%). $^1$H NMR ($D_2O$+NaOD, 500 MHz): δ 5.19 (s, 2H), 2.07 (s, 36H).

Catalytic Hydrogenation of $CO_2$

The catalytic reduction of $CO_2$ by 1, 2 and 3 was investigated under varied conditions that are summarized in Table 1. Entries 1-5 show selected results from other known systems for comparison. While rates of turnover frequency (TOF) as high as 348,000 $h^{-1}$ (Entry 5) and turnover number (TON) as high as 3,500,000 (Entry 4) have been reported, extraordinary pressures (5-6 MPa) combined with temperatures ranging from 120-200° C. are required to achieve them. High pressures and temperatures decrease the efficiency of an energy-storage system. By contrast, at 0.1 MPa of 1:1$H_2$:$CO_2$ gas and T=25° C., 2' afforded formate at a rate of 61 $h^{-1}$ and turnover number (TON) of 7,200 yielding 0.36 M formate (entry 6, pH=8.1); final concentrations of 0.66 M were obtained after 336 hours when 2 M $KHCO_3$ is used (Table 1, entry 8). This is an improvement of nearly an order of magnitude over a previous report of 7 $h^{-1}$ for 1' (entry 6), the only other catalyst that is active under ambient conditions. Rates and turnovers for 2' were increased to TOF=53,800 $h^{-1}$ and TON=up to 153,000, (1.70 M final formate) under pressurized conditions at relatively low temperature (Table 1, entries 9, 10 and 11, respectively). By comparison, 3 shows no reaction at room temperature after 8 hours (Table 1, Entry 14), and only 110 turnovers under pressurized conditions (Entry 9, T=50° C., P=1 MPa, 2 hrs). The change in the reaction rates between catalysts 2' and 3 clearly illustrates the effect of the ligand on the rate of catalytic $CO_2$ hydrogenation. As with all previously reported systems, elevated temperature and pressure is required for 3 to hydrogenate $CO_2$, while 2' proceeds at ambient conditions.

Catalytic Formate-Consumption and $H_2$ Production

The ability to store $H_2$ as a liquid is important because the energy density is greater than in the gas phase, and because liquid fuel is central to the current industrial infrastructure. Having established that 2' efficiently converts $CO_2$ to aqueous formate under basic conditions, the inventors examined the reverse reaction under acidic conditions. As discussed below, 2 ionizes to 2' near pH=3.74 and in the range 3<pH>5. As summarized in Table 2, when protonated, 2 catalyzes the release of $H_2$ and $CO_2$ (1:1) from aqueous $HCO_2H$/$HCO_2Na$ mixtures at record-breaking reaction rates. In contrast to other catalysts it requires no organic additives, and decomposes $HCO_2H$ completely (TON=20,000 at 60° C.; Table 2 Entry 2). Unprecedented catalytic activity (TON=308,000 at 80° C. and TOF=228,000 $h^{-1}$ at 90° C.) was measured in mixtures of $HCO_2Na$/$HCO_2H$ (Table 2, Entries 4-5). These values are the highest reported at this temperature, even for catalysts requiring additives. The liquid-to-gas conversion is quantitative in all cases, regardless of whether $HCO_2H$ or $HCO_2Na$ is used, although the latter reaction is significantly slower.

TABLE 2

Catalytic Decomposition of $HCO_2H$ by 1, and 2.

| Entry | Catalyst | Catalyst Conc., μM | Temp. | Total time, h | initial TOF$^a$ $h^{-1}$ | TON | Final [$HCO_2H$], M |
|---|---|---|---|---|---|---|---|
| 1 | 1$^b$ | 200 | 60 | 4 | 2,400 | 5,000 | 0 |
| 2 | 2$^b$ | 50 | 60 | 4 | 12,000 | 20,000 | 0 |
| 3 | 2 | 50 | 60 | 18 | 31,600 | 16,800 | 0.16 |

TABLE 1

Hydrogenation of $CO_2$ or Bicarbonate (1M $NaHCO_3$, pH = 8.4) in $H_2O$ (1:1 $H_2$:$CO_2$).

| Entry | Catalyst | Catalyst Conc., μM | Pressure MPa | Temp. °C. | Total time, h | initial TOF$^a$ $h^{-1}$ | TON | Final [HCOOH], M |
|---|---|---|---|---|---|---|---|---|
| 1 | [RhCl(η$^4$C$_8$H$_{12}$)]$_2$ | — | 2 | 25 | 22 | 52 | 1150 | — |
| 2 | RhCl$_3$ | — | 1 | 50 | 10 | 215 | 2150 | — |
| 3 | Ir(PNP)* | 2 | 5$^d$ | 200 | 2 | 150,000 | 300,000 | 0.6 |
| 4 | Ir(PNP)* | 0.2 | 6$^d$ | 120 | 48 | 73,000 | 3,500,000 | 0.7 |
| 5 | Ir(PNP')* | 0.0002 | 800 | 185 | 24 | 348,000 | 145,000 | |
| 6 | 1 | 50 | 0.1 | 25 | 24 | 7 | 92 | 0.005 |
| 7 | 2 | 50 | 0.1 | 25 | 336 | 61 | 7200 | 0.36 |
| 8 | 2$^b$ | 250 | 0.1 | 25 | 336 | 32 | 2640 | 0.66 |
| 9 | 2$^b$ | 10 | 4 | 50 | 8 | 15,700 | 153,000 | 1.53 |
| 10 | 2$^b$ | 2 | 5 | 80 | 2 | 53,800 | 79,000 | 0.16 |
| 11 | 2$^b$ | 40 | 3 | 50 | 48 | 9,400 | 42,500 | 1.70 |
| 12 | 2 | 50 | 1 | 25 | 2 | 3,050$^c$ | 6,100 | 0.305 |
| 13 | 3 | 250 | 0.1 | 25 | 8 | 0 | 0 | 0 |
| 14 | 3 | 50 | 1 | 50 | 2 | 55$^c$ | 110 | 0.055 |

$^a$Averaged rate for initial 1 h.
$^b$The reaction carried out in 2M $KHCO_3$.
$^c$average rate for entire reaction.
$^d$Total pressure at room temperature in 1M KOH (5 mL) and THF (0.1 mL).
*Indicates a PNP-type pincer ligand. See cited reference for structure.

TABLE 2-continued

Catalytic Decomposition of HCO₂H by 1, and 2.

| Entry | Catayst | Catalyst Conc., µM | Temp. | Total time, h | initial TOF$^a$ h$^{-1}$ | TON | Final [HCO₂H], M |
|---|---|---|---|---|---|---|---|
| 4 | 2 | 1.25 | 80 | 12 | 158,000 | 308,000 | 0.54 |
| 5 | 2 | 3.1 | 90 | 7 | 228,000 | 165,000 | 0.48 |

Reaction Conditions: 1M HCO₂H/HCO₂Na (1:1, pH = 3.6),
$^a$averaged rate for initial 5 to 15 min.
$^b$1M HCO₂H.

Recyclability and Pressurization Experiments

Figure 2:
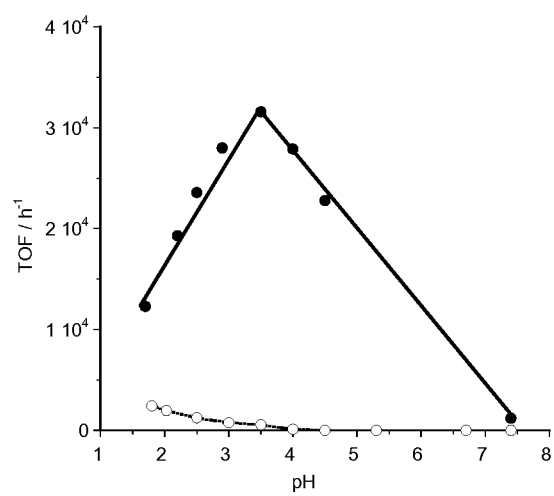
FIG. 2 shows the correlation between the rate of HCOO$^-$ consumption and pH for 1 (open circles) and 2 (closed circles) at 60° C. in 1M HCO$_2$H/HCO$_2$Na. A maximal rate is reached at ca. pH=3.6 for 2, while 1 shows decreasing activity as pH is increased.
Figure 3:
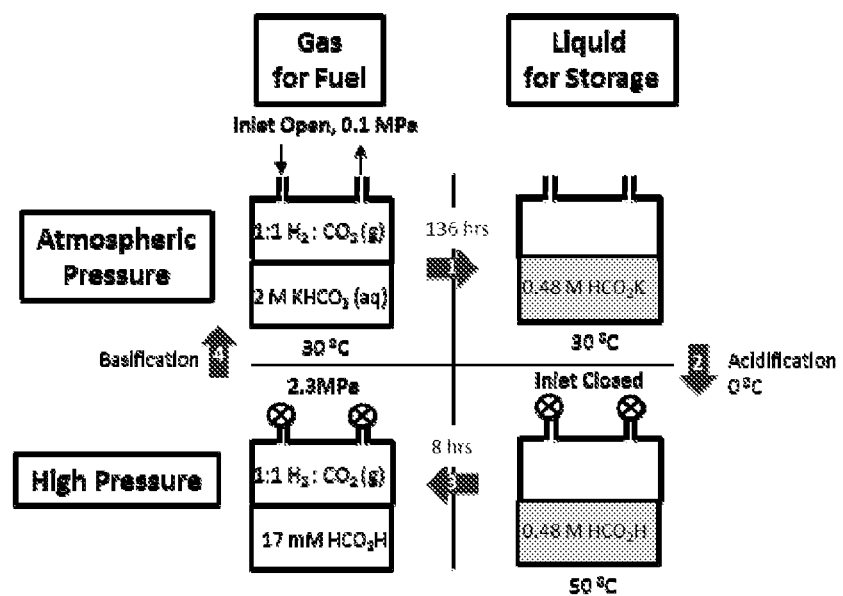
FIG. 3 shows the consecutive hydrogenation of $CO_2$ and decomposition of formic acid sequence. The vessel is at first opened to atmospheric conditions to store $H_2$, and then closed to release the gas under pressure: (1) hydrogenation of $CO_2$/bicarbonate; (2) acidification by addition of sulfuric acid; (3) decomposition of formic acid. The system can be regenerated by basification with KHCO$_3$ in step 4.

Varying the solution pH alters the HCO₂H:HCOO⁻ ratio. Plotting the rate versus pH shows that 2 produces H₂ best at pH=about 3.6 (FIG. 2), near the optimal pH of 3.8 for [Ir$^{III}$(Cp*)(H₂O)(bpym)Ru$^{II}$(bpy)₂](SO₄)₂ (bpy=2,2'-bipyridine) reported by Fukuzumi, S., Kobayashi, T. & Suenobu, T. "Unusually Large Tunneling Effect on Highly Efficient Generation of Hydrogen and Hydrogen Isotopes in pH-Selective Decomposition of Formic Acid Catalyzed by a Heterodinuclear Iridium-Ruthenium Complex in Water," *Journal of the American Chemical Society* 132, 1496-+(2010), and also near the ligand pKa. In contrast CO₂ hydrogenation is optimal near pH=about 8. pH as a trigger for H₂ storage and release by using consecutive CO₂-hydrogenation and HCO₂H decomposition sequences (FIG. 3) was studied.

In the first sequence (Step 1, FIG. 3) a solution of 2 in 2 M KHCO₃ (20 mL) was exposed to a constant flow of a 1:1 CO₂:H₂ mixture at ambient pressure (0.1 MPa, 30° C.) for 136 h to yield a 0.48 M formate solution, which corresponds to about 230 mL of absorbed liquid H₂. The reaction solution was then cooled by ice water and the pH of the solution was adjusted to pH=1.7 with 8 N sulfuric acid (Step 2 in FIG. 3). H₂ release was subsequently triggered by warming the solution to 50° C. in a closed glass autoclave, and resulted in a final pressure of 2.3 MPa of H₂:CO₂=1:1, with no detectable CO byproduct (Step 3, FIG. 3). As shown in Step 4, the sequence can be repeated by cooling the system by ice water and adjusting the pH with KHCO₃. The resulting solution gave a 0.38 M of formate as second cycle under same reaction conditions. The system, inclusive of metal organic frameworks, tank systems, and other metal hydrides, is capable of creating a pressurized H₂ system that has the additional advantage of recycling the same catalyst solutions.

Methods

All manipulations were carried out under an argon atmosphere using standard Schlenk techniques or in a glovebox, and all aqueous solutions were degassed prior to use. ¹H NMR and ¹³C NMR spectra were recorded on a Varian NOVA 400 and a Bruker Avance 400 spectrometers using sodium 3-(trimethylsilyl)-1-propanesulfonate (DSS sodium salt) as an internal standard. The X-Ray structure was determined using a Bruker Kappa Apex II diffractometer. pH values were measured on an Orion 3-Star pH meter with a glass electrode after calibration to standard buffer solutions. The evolved gas was measured at various intervals with a gastight syringe. H₂ was detected by a TCD (thermal conductivity detector) using an activated 60/80 carbon column and CO₂ and CO were detected using an FID equipped with a methaniser using a Porapak Q 80/100 column at 50° C. on a GL Science GC390 gas chromatograph. Formate was produced from research grade CO₂ (>99.999%) and H₂ (>99.9999%), or mixed gas (CO₂/H₂=1/1) through O₂ trap; formate-product concentrations were monitored by an HPLC on an anion-exclusion column (Tosoh TSKgel SCX(H⁺)) using aqueous H₃PO₄ solution (20 mM) as eluent and a UV detector (λ=210 nm).

[Cp*IrCl₂]₂ was prepared by refluxing a suspension containing a 2:1 mixture of hydrated IrCl₃: pentamethylcyclopentadiene (Cp*) in methanol for 48 hours. Complexes 1 and 3 were prepared according to literature procedures. See Himeda, Y. et al. pH-Dependent Catalytic Activity and Chemoselectivity in Transfer Hydrogenation Catalyzed by Iridium Complex with 4,4'-Dihydroxy-2,2'-bipyridine. *Chemistry-a European Journal* 14, 11076-11081 (2008) and Govindaswamy, P. et al. Mono and dinuclear rhodium, iridium and ruthenium complexes containing chelating 2,2'-bipyrimidine ligands: Synthesis, molecular structure, electrochemistry and catalytic properties. *Journal of Organometallic Chemistry* 692, 3664-3675 (2007). DFT calculations were performed using the Gaussian 09 Software Package with B3LYP functional and a CEP-121G basis set for Ir, and 6-31+G(d,p) for C, N, O, H.

Procedure for Catalytic Hydrogenation of CO₂/Bicarbonate at Atmospheric Conditions:

A degassed aqueous NaHCO₃ or KHCO₃ solution (20 mL) of the complex was stirred at atmospheric H₂:CO₂ (1:1). At appropriate intervals, samples were removed and analyzed by HPLC. The initial TOF was calculated from the initial part of the reaction (typically 30 min).

Procedure for Catalytic Hydrogenation of CO₂/Bicarbonate at Pressurized Conditions:

A degassed aqueous NaHCO₃ or KHCO₃ solution (50 mL) of catalyst was stirred in a 100 mL stainless steel reactor equipped with a sampling device. The reactor was heated, and then was filled to the desired pressure with CO₂:H₂=1:1. Samples were removed at appropriate intervals (typically 5, 15, 30, 60, 90 and 120 min.) and analyzed by HPLC. The initial TOF was calculated from the initial part of the reaction (typically 30 min).

Procedure for Catalytic Decomposition of Formic Acid/Formate:

Typically, a freshly prepared 5 mM solution of catalyst (100 µL, 0.5 µmmol) was added to a deaerated aqueous HCO₂H/HCO₂Na solution, and the mixture was stirred at the desired temperature. The volume of gas evolution was determined by a gas meter (Shinagawa Corp., W-NK-05). The initial TOF was calculated from the initial part of the reaction with the exception of the brief induction period.

Procedure for Catalytic Decomposition of Formic Acid/Formate in Closed System:

Typically, a freshly prepared 5 mM solution of catalyst (100 µL, 0.5 µmol) was added to a deaerated aqueous HCO₂H/HCO₂Na solution in a 10 mL glass autoclave, and the mixture was stirred at the desired temperature. The pressure in the reactor was measured by a digital pressure gauge (NAGANO KEIKI Co., LTD. GC64).

Procedure for Hydrogenation of CO₂ at Ambient Conditions and Decomposition of Formic Acid in Closed System:

As described above in the procedure for the hydrogenation of CO₂ at atmospheric conditions, the reaction was carried out using 2 (5 mmol) in 2 M KHCO₃ (20 mL) at 30° C. for 136 h. The resulting 0.48 M formate solution was cooled to 0° C., and then was adjusted to pH 1.7 by the addition of a deaerated 8 N H₂SO₄. The supernatant was transferred to the glass autoclave of the reactor, sealed for pressurization and then stirred at 50° C. The pressure in the reactor was measured by a digital pressure gauge (NAGANO KEIKI Co., LTD. GC64, Figure S6). At the end of the reaction, the evolved gas was analyzed by GC and concentration of formic acid in the reaction solution was analyzed by HPLC. In order to recycle the catalyst, KHCO₃ (4.0 g, 40 mM) was added to the reaction solution after returning the vessel to atmospheric pressure.

The resulting solution was stirred at atmospheric $H_2:CO_2$ (1:1) and the cycle was continued as described in line 1 of this procedure.

We claim:

1. A ligand represented by formula I below:

wherein X is independently OH, SH, or $NH_2$.

2. The ligand of claim 1, wherein X is OH.

3. A catalyst of formula II below:

wherein:
X is independently OH, SH, or $NH_2$;
M independently represents Ni, Pd, Pt, Co, Rh, Ir, Fe, Ru, or Os;
Y independently represents a coordinating solvent species or solvent molecule selected from the group consisting of halide, water, hydroxyl, carbonyl, acetonitrile, dimethylformamide, and dimethylsulfoxide;
L independently represents Cp, Cp*, or an unsubstituted or substituted n-arene;
m and c independently represent integers from 1 to 6;
n represents 0, +1, +2, +3, +4, +5, or +6;
a represents an integer from 0 to 6;
B represents an anion; and
m×n=a×c.

4. The catalyst of claim 3, wherein X is OH.

5. The catalyst of claim 3, wherein M is Ir.

6. The catalyst of claim 3, wherein Y is Cl.

7. The catalyst of claim 3, wherein L is Cp, Cp*, benzene, or cymene.

8. A method of hydrogenating $CO_2$ to form formic acid and/or a salt thereof comprising reacting $CO_2$ and $H_2$ in water in the presence of a catalyst of formula II below and a base:

wherein:
X is independently OH, SH, or $NH_2$;
M independently represents Ni, Pd, Pt, Co, Rh, Ir, Fe, Ru, or Os;
Y independently represents a coordinating solvent species or solvent molecule selected from the group consisting of halide, water, hydroxyl, carbonyl, acetonitrile, dimethylformamide, and dimethylsulfoxide;
L independently represents Cp, Cp*, or an unsubstituted or substituted n-arene;
m and c independently represent integers from 1 to 6;
n represents 0, +1, +2, +3, +4, +5, or +6;
a represents an integer from 0 to 6;
B represents an anion; and
m×n=a×c.

9. The method of claim 8, wherein the reaction occurs at ambient pressure and ambient temperature.

10. The method of claim 8, wherein the reaction occurs between a minimum of 0 MPa and a maximum of 100 MPa.

11. The method of claim 8, wherein the reaction occurs between a minimum of 0° C. and a maximum of 200° C.

12. The method of claim 8, wherein X is OH.

13. The method of claim 8, wherein M is Ir.

14. The method of claim 8, wherein Y is Cl.

15. The method of claim 8, wherein L is Cp, Cp*, benzene, or cymene.

16. The method of claim 8, wherein the reaction occurs in the absence of organic additives.

17. The method of claim 8, wherein the reaction occurs at a minimum pH of 5.

18. The method of claim 17, wherein the reaction occurs at a maximum pH of 10.

19. A method of dehydrogenating formic acid and/or a salt thereof to form $H_2$ and $CO_2$ comprising reacting formic acid and/or a salt thereof in the presence of a catalyst of formula II below:

wherein:
X is independently OH, SH, or $NH_2$;
M independently represents Ni, Pd, Pt, Co, Rh, Ir, Fe, Ru, or Os;

Y independently represents a coordinating solvent species or solvent molecule selected from the group consisting of halide, water, hydroxyl, carbonyl, acetonitrile, dimethylformamide, and dimethylsulfoxide;

L independently represents Cp, Cp*, or an unsubstituted or substituted n-arene;

m and c independently represent integers from 1 to 6;

n represents 0, +1, +2, +3, +4, +5, or +6;

a represents an integer from 0 to 6;

B represents an anion; and m×n=a×c.

20. The method of claim 19, wherein X is OH.
21. The method of claim 19, wherein M is Ir.
22. The method of claim 19, wherein Y is Cl.
23. The method of claim 19, wherein L is Cp, Cp*, benzene, or cymene.
24. The method of claim 19, wherein the reaction occurs at ambient pressure and ambient temperature.
25. The method of claim 19, wherein the reaction occurs between a minimum of 0° C. and a maximum of 200° C.
26. The method of claim 19, wherein the reaction occurs between a minimum of 0 MPa and a maximum of 100 MPa.
27. The method of claim 19, wherein the reaction occurs in the absence of organic additives.
28. The method of claim 19, wherein the reaction occurs at a maximum pH of 8.
29. A method of reversibly storing hydrogen, the method comprising the steps of:

a) providing $H_2$ and $CO_2$ in water;

b) adjusting the pH to a minimum of 5 at a temperature and pressure sufficient to produce formic acid and/or a salt thereof; and c) adjusting the pH to a maximum of 8 at a temperature and pressure sufficient to dehydrogenate the formic acid and/or a salt thereof to produce $H_2$ and $CO_2$; wherein steps b) and c) are conducted in the presence of a catalyst of formula II below:

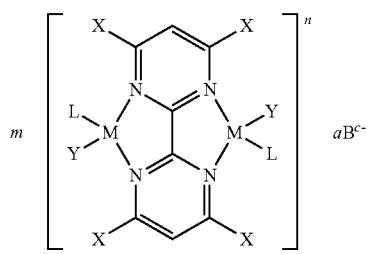

wherein:

X is independently OH, SH, or $NH_2$;

M independently represents Ni, Pd, Pt, Co, Rh, Ir, Fe, Ru, or Os;

Y independently represents a coordinating solvent species or solvent molecule selected from the group consisting of halide, water, hydroxyl, carbonyl, acetonitrile, dimethylformamide, and dimethylsulfoxide;

L independently represents Cp, Cp*, or an unsubstituted or substituted n-arene;

m and c independently represent integers from 1 to 6;

n represents 0, +1, +2, +3, +4, +5, or +6;

a represents an integer from 0 to 6;

B represents an anion; and m×n=a×c.

30. The method according to claim 29, wherein steps a), b), and c) are conducted in a closed reaction vessel.
31. The method according to claim 30, wherein steps b) and c) are repeated.
32. The method of claim 29, wherein X is OH.
33. The method of claim 29, wherein M is Ir.
34. The method of claim 29, wherein Y is Cl.
35. The method of claim 29, wherein L is Cp, Cp*, benzene, or cymene.
36. The method according to claim 30, wherein step b) occurs at ambient pressure and ambient temperature.
37. The method according to claim 30, wherein the pH in step b) is adjusted to a maximum of 10.
38. The method according to claim 37, wherein the pH in step b) is adjusted to about 8.
39. The method according to claim 29 occurring in the absence of organic additives.
40. The method according to claim 31, wherein the temperature in step c) is adjusted to between a minimum of 0° C. and a maximum of 200° C.

* * * * *

UNITED STATES PATENT AND TRADEMARK OFFICE
CERTIFICATE OF CORRECTION

PATENT NO. : 9,095,846 B2 Page 1 of 2
APPLICATION NO. : 14/240587
DATED : August 4, 2015
INVENTOR(S) : Hull et al.

It is certified that error appears in the above-identified patent and that said Letters Patent is hereby corrected as shown below:

IN THE SPECIFICATION:

Column 2, line 41,
   now reads: "n-arene"
   should read: -- π-arene --

Column 4, line 3,
   now reads: "n-arene"
   should read: -- π-arene --

Column 4, line 36,
   now reads: "n-arene"
   should read: -- π-arene --

Column 5, line 1,
   now reads: "n-arene"
   should read: -- π-arene --

Column 5, line 10,
   now reads: "$5^+$ or 6', respectively."
   should read: -- $5^+$ or $6^+$, respectively. --

Column 5, line 44,
   now reads: "LiHCO$_3$, NaHCO3, and"
   should read: -- LiHCO$_3$, NaHCO$_3$, and --

Column 10, line 16,
   now reads: "in in iPrOH"
   should read: -- in *i*PrOH --

Signed and Sealed this
Twenty-fourth Day of May, 2016

Michelle K. Lee
*Director of the United States Patent and Trademark Office*

CERTIFICATE OF CORRECTION (continued)
U.S. Pat. No. 9,095,846 B2

IN THE SPECIFICATION:

Column 10, line 19, now reads: "iPrOH"

should read: -- *i*PrOH --

Column 16, line 23, now reads: "n-arene"

should read: -- π-arene --

Column 17, line 6, now reads: "n-arene"

should read: -- π-arene --

Column 18, line 12, now reads: "n-arene"

should read: -- π-arene --